United States Patent [19]
Khouri

[11] Patent Number: 5,676,634
[45] Date of Patent: Oct. 14, 1997

[54] METHOD AND APPARATUS FOR SOFT TISSUE ENLARGEMENT WITH BALANCED FORCE APPLIANCE

[75] Inventor: Roger K. Khouri, St. Louis, Mo.

[73] Assignee: Khouri Biomedical Research, Inc., St. Louis, Mo.

[21] Appl. No.: 516,623

[22] Filed: Aug. 18, 1995

Related U.S. Application Data

[63] Continuation-in-part of Ser. No. 504,640, Jul. 20, 1995, which is a continuation of Ser. No. 220,186, Mar. 30, 1994, Pat. No. 5,536,233.

[51] Int. Cl.$^6$ ........................................................ A61F 5/00
[52] U.S. Cl. .................................................. 600/38; 601/14
[58] Field of Search ....................... 600/38; 128/897–98; 601/14, 11, 6–13; 602/42–53

[56] References Cited

U.S. PATENT DOCUMENTS

| | | |
|---|---|---|
| 936,434 | 10/1909 | Eganhouse . |
| 1,312,619 | 8/1919 | D'Orsay . |
| 2,616,417 | 11/1952 | Holbrook . |
| 3,382,867 | 5/1968 | Reaves . |
| 3,631,853 | 1/1972 | Burdette, Jr. . |
| 3,785,369 | 1/1974 | Tallent . |
| 4,856,498 | 8/1989 | Osbon . |
| 4,856,499 | 8/1989 | Kelly . |
| 5,234,401 | 8/1993 | Yamanaka . |

FOREIGN PATENT DOCUMENTS

WO 91/17727  11/1991  WIPO .

OTHER PUBLICATIONS

Copy of *Enlargement Book*, ©1990 Topco Books.
Copy of *An Anthology Of Plastic Surgery*, edited by Harry Hayes, Jr., M.D., specifically Section 6 entitled "Quackery and Nostrums", Aspen Publishers, Inc., 1986, pp. 163–175.
Article entitled "The Tension–Stress Effect on the Genesis and Growth of Tissue—Part 1. The Influence of Stability of Fixation and Soft–Tissue Preservation" by Gavrll A. Ilizarov, AM., M.D., Ph.D., from *Clinical Orthopaedics and Related Research*, from Section III, entitled Basic Science An d Pathology, No. 238, Jan. 1989, pp. 249–281.
Article entitled "The 'Niplette': an instrument for the non–surgical correction of inverted nipples" by D.D. McGeorge, from *British Journal Of Plastic Surgery* 1994, pp. 46–49.
Copy of *How To Enlarge Your Penis*, ©1988 House One, expurgated version.
Brochure entitled "Nipple Enlargement System" by Joel Kaplan, Ph.D., 1993.
Article entitled "The Ilizarov Technique: A method To Regnerate Bone And Soft Tissue" by Dror Paley, M.D., et al., pp. 1–41.
Article entitled "The Callotasis Method of Limb Lengthening" by Roberto Aldegheri, M.D., et al., from *Clinical Orthopaedics and Related Research*, No. 241, Apr. 1989, pp. 137–145.
Article entitled "Histophathology of Human Expanded Tissue" by Krystyna A. Pasyk, M.D. et al., from *Clinics in Plastic Surgery*, vol. 14, No. 3, Jul. 1987, pp. 435–445.
Article entitled "The Expansion of an Area of Skin by Progressive Distention of Subcutaneous Balloon—Use of the Method for Securing Skin for Subtotal Reconstruction of the Ear", by Charles G. Neumann, M.D., from *Plastic And Reconstructive Surgery* Feb., 1957, pp. 124–130.

(List continued on next page.)

*Primary Examiner*—John P. Lacyk
*Attorney, Agent, or Firm*—Howell & Haferkamp, L.C.

[57] ABSTRACT

An apparatus and method for enlargement of soft tissue such as breasts or a penis is comprised of a dome configured to fit over the area of desired augmentation. The dome has a rim with a surface area sized to prevent excessive contact pressure to the skin when a suction force of sufficient magnitude to cause enlargement of the soft tissue is applied to the soft tissue by the dome.

30 Claims, 2 Drawing Sheets

OTHER PUBLICATIONS

Article entitled "Tissue Expansion in Soft–Tissue Reconstruction", by Chedomir Radovan, M.D., from *Plastic and Reconstructive Surgery*, Oct. 1984, pp. 482–492.

Article entitled "Elongation of Peripheral Nerve and Viscera Containing Smooth Muscle" by Ernest K. Manders, M.D., et al., from *Clinics in Plastic Surgery*, vol. 14, No. 3, Jul. 1987, pp. 551–562.

Article entitled "Rapid Elongation of Arteries and Veins in rats with Tissue Expander" by G. Björn Stark, M.D., et al., from *Plastic And Reconstructive Surgery*, Oct. 1987, pp. 570–581.

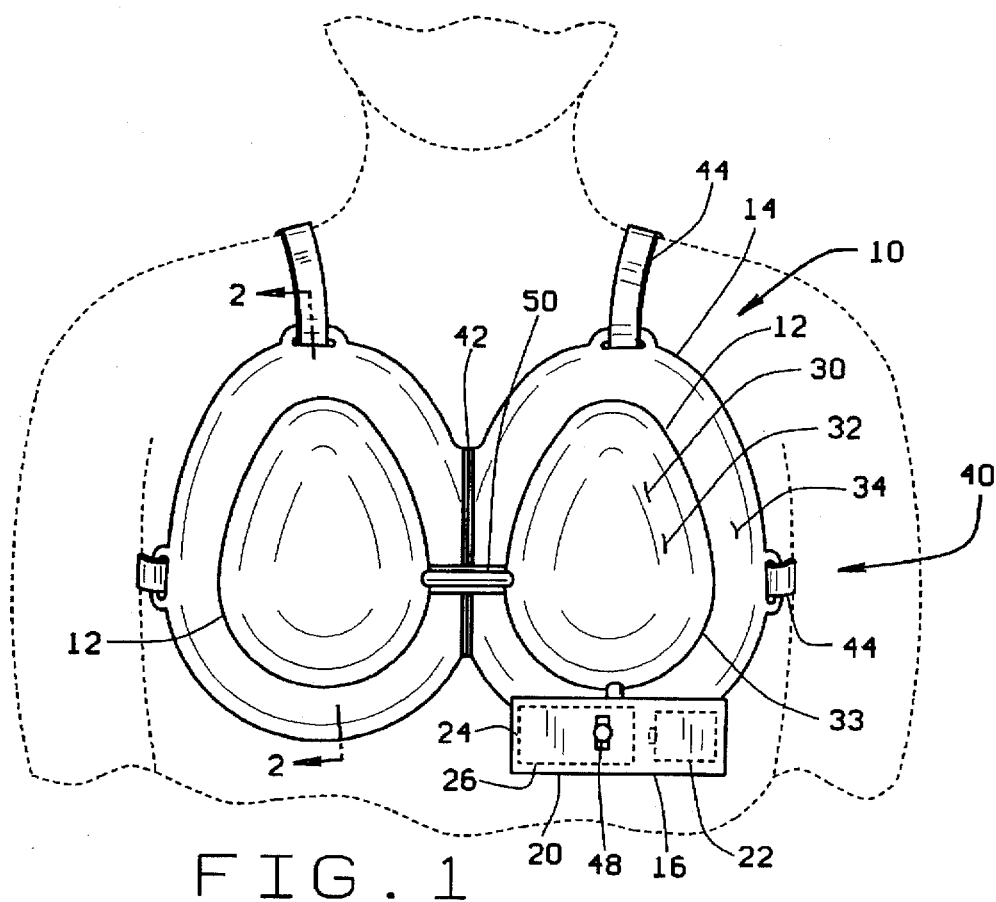
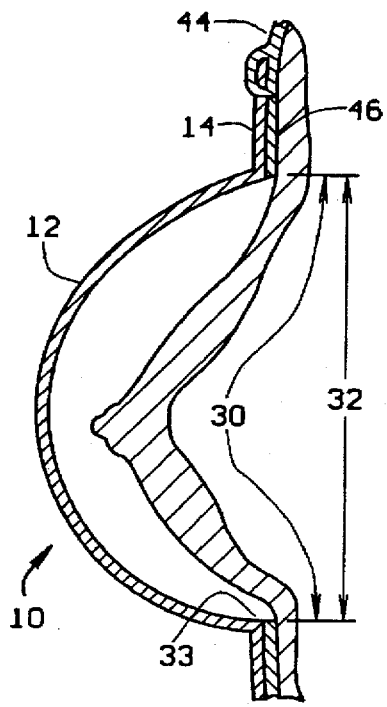
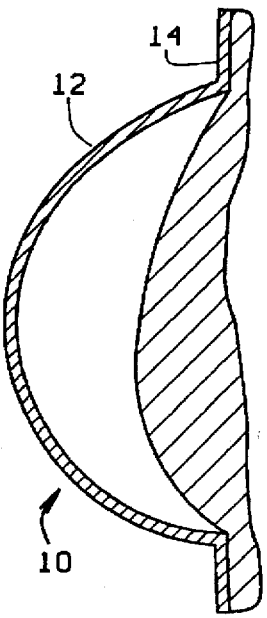
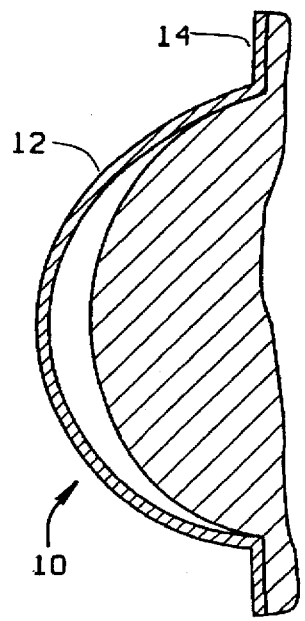

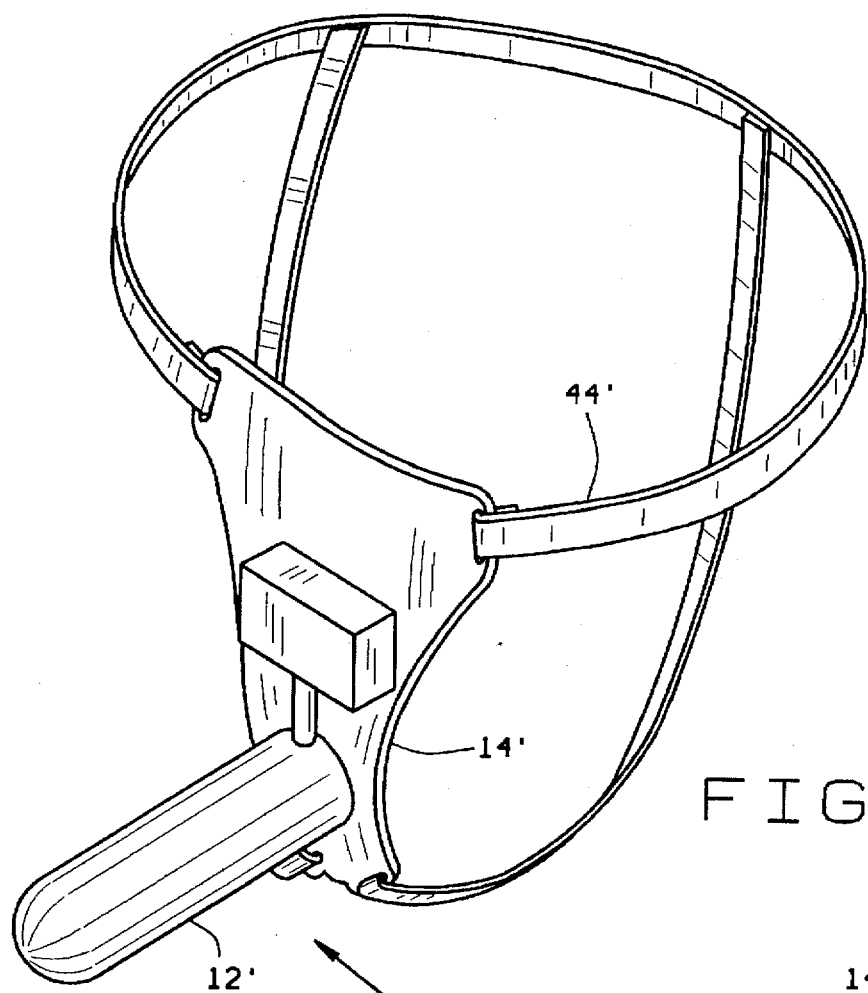
FIG. 5
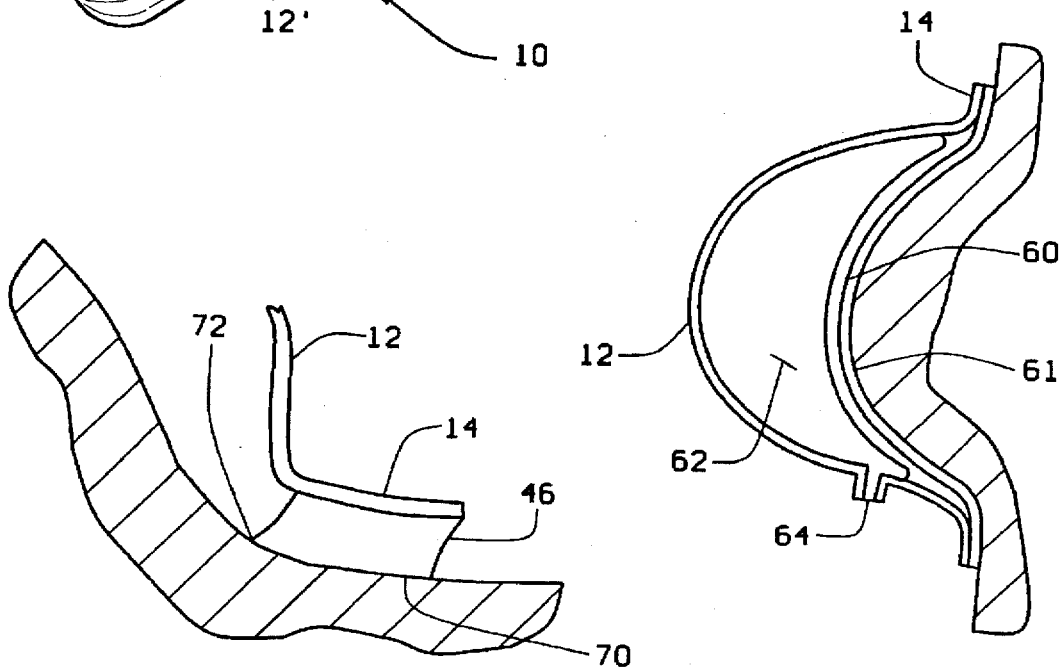
FIG. 7
FIG. 6

METHOD AND APPARATUS FOR SOFT TISSUE ENLARGEMENT WITH BALANCED FORCE APPLIANCE

This application is a continuation-in-part of a U.S. patent application Ser. No. 08/504,640 filed Jul. 20, 1995, entitled "Method and Apparatus for Soft Tissue Enlargement by Distractive Force" which was a continuation of U.S. patent application Ser. No. 08/220,186 filed Mar. 30, 1994, now U.S. Pat. No. 5,536,233 entitled "Method and Apparatus for Soft Tissue Enlargement".

BACKGROUND AND SUMMARY OF THE INVENTION

There are numerous instances where persons desire enlargement of the soft tissues in their bodies. One such instance is for the replacement of one or both breasts amputated during a mastectomy in order to restore physiological symmetry and psychological well-being. Other instances are for correction of natural abnormalities such as dimpling. Still other instances are for augmentation of physical attributes to improve cosmetics and self-esteem. These latter soft tissue enlargements are principally directed to breast enlargement in females and penis enlargement in males.

Prosthetic implants have been developed for insertion below the skin. However, the severity of the potential complications including scarring, implant rupture, capsular contracture, necrosis and implant migration as well as the recent adverse publicity thereof have significantly reduced the desirability of these implants. Thus, there is a societal need for other means to obtain soft tissue enlargement.

Some soft tissue enlargements occur naturally. For instance, during pregnancy, the skin over a woman's abdominal region enlarges approximately nine times its previous area to accommodate the fetus without a proportional decrease in skin thickness. In other words, the abdominal skin tissue actually enlarges and does not merely stretch during pregnancy. Similarly, the skin will expand to accommodate any growth under the skin.

In the past, plastic surgeons have used this phenomena to their advantage to expand skin in order to accommodate prosthetic implants. To conduct this procedure, the surgeon inserts a balloon beneath the skin in the area where additional skin is desired. By progressively expanding the balloon, the skin first stretches and eventually actually grows to accommodate the increased volume underneath it. When the desired amount of skin is formed, the balloon is deflated and removed, and the implant is inserted into the cavity left by the balloon. Similar methods have been used by native African tribes to enlarge lips, nostrils, and earlobes.

Other surgical techniques have used tissue expansion to achieve other types of soft tissue growth. For instance, balloons have been successfully expanded underneath nerves, veins, tendons, and the like to thereby elongate these tissues to repair damage and alleviate various abnormalities.

A more advanced surgical method is known as callotasis or limb lengthening. This method comprises cutting the bone about its periphery at the location where lengthening is desired, leaving the tissues inside and around the bone intact. Brackets are attached to the bone on each side of the separation, and the bone segments are slowly pulled away from one another while remaining integral over a period of several months. Not only does this cause the mended bone to be longer, but also the soft tissue surrounding the bone actually grows to accommodate the increased limb length. Similar methods have been used by African native tribes to lengthen necks for cosmetic purposes.

Each of these above-mentioned apparatuses and methods requires an invasive surgical technique to accomplish the soft tissue expansion. Invasive techniques increase the likelihood of the complications associated with the procedure including those mentioned above with respect to implant surgery. In addition, the expense of surgery precludes many persons having their abnormalities corrected or physical attributes enhanced.

Other soft tissue enlargement techniques have been developed which use other mechanisms to cause the enlargement. For instance, an instrument and technique have been developed for the non-surgical correction of inverted nipples due to short lactiferous ducts. The instrument is comprised of a cup having an internal volume shaped like that of the final desired nipple. The user places the cup over the inverted nipple, pumps the air out of the cup with a syringe and adjusts the vacuum within the cup using a check valve to just below the threshold of discomfort. Thus attached, the device puts the lactiferous ducts in tension and extends them sufficiently after two to three months of wear at 8–12 hours per day.

Although this device is sufficient for its intended purpose, it is not suitable for general soft tissue enlargement. Laceration and contusion can occur if too strong of a suction is applied to soft tissue. As the pressure within the inverted nipple instrument is not regulated, contusion or laceration can occur. When a vacuum is developed within the cup of the instrument, an equal and opposite force is applied to the patient about the rim of the cup. Excessive contact forces against the patient can cause ulceration, laceration, and contusions. As the contact forces are not regulated in the nipple instrument, these further complications also can occur. In addition, general soft tissue enlargement is not feasible with the instrument due to the size and shape of the cup.

Another prior art device is disclosed in U.S. Pat. No. 936,434 as a device for enlarging a woman's breasts. This device included a pair of cups for placement on the breasts and a pump for exhausting the air from between the cups and breasts. However, this patent provides no teaching as to the pressures to be used, the potential danger to the skin tissues, or any suggestions as to how the device is to be retained in place during use. Apparently, the device is used in a clinical setting and is not suitable for long term wear such as for 8–10 hours. As the patent suggests that the vacuum acts to cause the veins and arteries to engorge, thereby nourishing the breasts, it is clear that the patentee is suggesting that the breast tissue actually expands through this expansion of blood vessels alone. This patent has been the subject of ridicule by at least one medical authority. See "An Anthology Of Plastic Surgery" edited by Harry Hayes, Jr., M.D., Section 6, "Quackery and Nostrums" pub. 1986 by Aspen Publishers, Rockville, Md.

Finally, another prior art device although notorious is worthy of note. This device is commonly referred to as a penis pump and is sold primarily as a novelty as its long-term enlargement efficacy has never been proven and is in fact universally disclaimed by its distributors. The device is comprised of a cylinder having one open end into which the penis is inserted and a pump attached to it such that a vacuum can be created within the cylinder. Not only does this device have the same drawbacks as the nipple instrument with respect to potential complications, but also it is unlikely that sufficient vacuum can be maintained by the device to cause any notable long-term soft tissue enlargement. Further, this device is apparently designed to accomplish two tasks unrelated to enlargement. First, the device is used for stimulation and sexual gratification. Second, the device is used to promote erection by drawing blood into the penis.

Most of these prior art devices and methods have failed to achieve long term soft tissue enlargement while preventing damage to the soft tissue being enlarged, as well as surrounding tissue. As disclosed and claimed in the parent application noted above, the inventor herein has succeeded in designing and developing a new generalized method and apparatus for soft tissue enlargement which prevents damage to soft tissue. The apparatus used for this enlargement is comprised of a rigid, fluid-impervious dome having a rim about its periphery and a vacuum pump for reducing pressure within the dome. The rim has sufficient surface area such that the pressure applied to the patient by the rim is less than or equal to the negative pressure applied to the soft tissue under the dome. In the parent application, one specific teaching to achieve this balanced force utilized a rim with substantially the same cross-sectional area as the normal area of the dome. Thus, as long as pressure within the dome is regulated to a limit below which medical complications will not occur, the opposing contact pressure against the patient is below this threshold as well. With this approach, damage is avoided not only to the soft tissue being enlarged, but the surrounding tissue as well. In the preferred embodiment of the apparatus, the vacuum pump has a self-contained power source. In addition, a pressure sensor and servomechanism control the pump such that the vacuum within the dome is maintained at a magnitude less than 35 mmHg. Variant embodiments may be configured to fit over and enlarge a human breast, a human penis, or any other desired area.

In implementing the device of the present invention, the inventor intends that it be capable of achieving its therapeutic effect without creating any long term tissue necrosis from use. In other words, a vacuum must be applied to the desired area to achieve the therapeutic effect for sufficient periods of time without applying too great a vacuum or contact pressure which will damage the underlying tissue. As considered from this generalized approach, one of ordinary skill in the art would understand the inventor's teaching to include the idea of providing a smaller vacuum pressure within the dome and balancing that smaller vacuum with a rim having a surface area less than the normal area of the dome, thereby creating a greater contact pressure which is still within acceptable limits. Still another approach which may very well provide a therapeutic effect would be to cycle the vacuum in the dome such that it is applied for periods of time at elevated levels and relaxed levels so that the rim might also have a cross-sectional area less than the normal area of the dome, but yet avoid creating any tissue necrosis. The cycling of the vacuum pressure in the dome could be readily achieved in an automatic manner by appropriately programming the vacuum pump and regulator. Therefore, the invention should be understood as being limited only by the current medical understanding of the causative effects of pressure sores and other tissue damage by an applied pressure or vacuum.

It is well recognized in the medical literature that decubitus ulcers are caused by unrelieved external pressure that occludes blood flow and results in tissue necrosis. In recognition of this fact, these ulcers are called pressure sores. The average capillary pressure in human skin is around 15–20 mmHg. E. M. Landis, *Micro-Injection Studies of Capillary Blood Pressure in Human Skin*, 15 Heart 209–228, (1930). For convenience, 20 mmHg will be used to describe this pressure throughout the remainder of this description. However, it should be understood that pressures below 20 mmHg may also be used without departing from the scope of this invention and that these lower pressures may provide additional margins in preventing damage to tissues. Therefore, the local application of an external pressure up to 20 mmHg will not collapse capillaries adjacent the location of the applied pressure and thus will not disturb the circulation. Therefore, local application of contact pressures less than or equal to 20 mmHg are well tolerated for prolonged periods of time. This tolerance has been confirmed by the inventor through use of a prototype which did not cause adverse effects after many hours of continuous use as long as the pressure under the rim remained below or around 20 mmHg.

Pressures greater than 20 mmHg will occlude the capillaries and stop tissue perfusion. Tissues can tolerate short periods of ischemia, but if the pressure is continuous and perfusion is not restored within a relatively short period of time, tissue damage will ensue. "The time factor is thus more important than pressure intensity". A pressure of 100 mmHg will lead to pathologic changes after only two hours. T. Hussain, *An Experimental Study of Some Pressure Effects on Tissues, with Reference to the Bed-Sore Problem*, 66 J. Path. Bact. 347–358, (1953).

The experimental results of additional investigators can be used to develop a safe time-pressure curve above which tissue damage will ensue. For instance, 20 mmHg is well tolerated for prolonged periods of time, but 40 mmHg will lead to tissue injury if the pressure is not relieved for 13 hours. The injury is more severe if the pressure is 60 mmHg, and even greater injury will result with a pressure of 100 mmHg after shorter periods of time. O. Lindan, *Etiology of Decubitus Ulcers: An Experimental Study*, 42 Arch. Phys. Med. Rehab. 774–783, (1961). Similarly, a pressure of 70 mmHg, if unrelieved, will lead to pathologic changes after 2 hours. However, if the pressure is intermittent, applied 5 minutes on, and 5 minutes off, there is no pathologic tissue changes. M. Kosiak, *Etiology of Decubitus Ulcers*, 42 Arch. Phys. Med. Rehab. 19–29, (1961).

These findings are consistent with the clinical testing of the prototype of the breast device. It was found that a continuous pressure under the rim of 40 mmHg could be tolerated for only one hour by healthy volunteers. After one hour, the volunteers started to complain of pain which is the warning sign of impending tissue damage. Higher pressures led to pain under the rim after even shorter periods of time. Lower pressures around 30 mmHg led to pain after 4 hours. However, if the pressure is allowed to cycle, that is if it is dropped down to 0–20 mmHg to allow the tissues to temporarily reperfuse for a few minutes, higher peak pressures can be tolerated. The higher the peak pressures, the shorter they are tolerated and the longer the low pressure part of the cycle needs to be to allow the tissues to recuperate.

Therefore, pressures under the rim greater than 20 mmHg can only be tolerated if there is a means to continuously cycle the pressure peaks on and off allowing for tissue re-perfusion during the off periods. The higher the peaks, the shorter the pressures are tolerated and the longer the period of low pressure recuperation needs to be.

From the above experimental animal data and human study, the inventor concludes that 20 mmHg is the highest pressure that can be safely tolerated under the rim on a prolonged basis. Higher pressures can only be applied intermittently, and then cycled down to less than 20 mmHg.

The method of use is comprised of the steps of attaching the dome to the location of desired enlargement, and creating a vacuum within the dome. In the continuous application method in which the vacuum is applied at pressures that can be withstood continuously, the vacuum should be maintained for a minimum of eight hours per day and results should be sufficient after several months.

As indicated by the summary of the medical literature given above, the present invention may also be used in alternative methods in keeping within the scope of the inventor's concept. For example, the device might have a rim cross-sectional area substantially less than the normal area of the dome and be used in either of two methods. In a first method, a somewhat lower vacuum pressure may be induced in the dome such that the opposing contact pressure under the rim may be maintained at bearable pressures for extended periods of time and yet provide a therapeutic effect. Alternatively, the vacuum in the dome may be regulated in a routine which provides somewhat higher vacuum pressures in the dome for shortened periods of time separated by periods of lower vacuum pressures to allow tissue reperfusion. In other words, alternating cycles of high vacuum, tissue reperfusion, high vacuum, tissue reperfusion, etc., may achieve a therapeutic effect in enlarging the soft tissues. With either of these methods, the rim may have a cross-sectional area substantially less than the normal area of the dome.

In an alternate embodiment to the present invention, the dome may include a flexible sheet attached about the rim and spanning the dome. The sheet may be applied to the desired soft tissue with an adhesive, and the vacuum may be applied between the dome and the sheet to introduce a tensile force to the surface of the soft tissue so as to pull the soft tissue away from the body. The adhesive may comprise typical adhesives or glues, as well as, sticky gels or sheets of double-sided adhesive tapes. Further, the adhesive may be an adhesive substance embedded in the sheet or in the rim of the dome.

In implementing any of the embodiments of the present invention, the inventor has found that it is desirable to provide a gasket around the rim of the dome which has the ability to distribute the shearing forces generated between the skin and rim as the tensile force is applied. In one embodiment, this is achieved by providing a rim made of silicone gel which has a thickness sufficient to allow its surface adjacent the skin to shift laterally with respect to the dome. In this way, the shearing force is distributed along virtually the entirety of its contact surface and even beyond the periphery of the rim. Thus, the shearing force is not concentrated as a high contact stress at the edge of the rim adjacent the pressurized area under the dome. As an alternative to a gel-like rim, the inventor has also considered the use of a balloon-like or inflated rim as specific embodiments of this aspect of the invention. Other configurations and constructions would be suitable, it only being desired to provide for a relative lateral shift between the dome and the surface of the rim which contacts the soft tissue as the vacuum is applied to thereby distribute the shearing force across the surface of the rim and beyond.

While the practical advantages and features of the present invention and method have been briefly described above, a greater understanding of the novel and unique features of the invention may be obtained by referring to the drawings and Detailed Description of the Preferred Embodiment which follow.

BRIEF DESCRIPTION OF THE DRAWINGS

FIG. 1 is a front elevation view of the soft tissue enlargement apparatus of the present invention, showing the breast augmentation embodiment;

FIG. 2 is a cross-sectional view of the breast enlargement embodiment taken in the plane of line 2—2 of FIG. 1;

FIG. 3 is a cross-sectional schematic of a dome and soft tissue in the early stages of enlargement;

FIG. 4 is a cross-sectional schematic of a dome and soft tissue in the latter stages of enlargement;

FIG. 5 is an orthographic projection of the penile augmentation embodiment of the present invention;

FIG. 6 is a cross-sectional schematic of a fourth alternate embodiment wherein a flexible sheet which may be bonded to the soft tissue spans the rigid dome to prevent leakage between the dome and the skin; and FIG. 7 is a cross-sectional diagram of an alternate embodiment wherein a flexible rim gasket is used to distribute the forces along the rim.

DETAILED DESCRIPTION OF THE PREFERRED EMBODIMENT

One embodiment of the soft tissue enlargement apparatus 10 is generally comprised of a dome 12 having a rim 14 and a vacuum pump assembly 16 for creating a vacuum within the dome. Although the vacuum pump assembly 16 may be a separate hand-held pump in one variant embodiment, in the preferred embodiment the vacuum pump assembly 16 is a self-contained vacuum pump 20 with an independent power source 22, pressure sensor 24, and servomechanism 26 for driving, regulating and controlling the vacuum pump 20.

Regulation of the vacuum within the dome is essential to prevent contusions caused by rupturing capillaries adjacent the surface of the skin. Medical data suggest that these contusions will not occur if vacuum within the dome is maintained at less than 20 mmHg. Thus, the vacuum pump 20 must be regulated to control the vacuum within the dome to within this limit. In addition, skin ulceration can occur if excessive contact pressures are applied thereto. Medical data suggest that a contact pressure less than 20 mmHg may be applied indefinitely without such ulceration. However, contusions may occur due to positive contact pressures upon the skin at pressures above this ulceration limit. The preferred embodiment of the present invention was developed with these limits in mind and will not apply a vacuum greater than 20 mmHg or constant contact pressure greater than 20 mmHg.

Several forces are developed within the dome and about the rim as a result of evacuating air from the dome. A suction or tensile force $F_s$ is developed within the dome 12 equal to the vacuum pressure $P_1$ multiplied by the enclosed tissue surface area 30, $A_s$. The vector sum of the tensile force upon the tissue surface area 30 may be called the normal force $F_1$ and is equal to the vacuum pressure multiplied by the normal area 32, $A_1$ of the dome opening, i.e., the projected area bounded by the periphery 33, or $F_1=P_1A_1$. An opposing force $F_2$ is imposed on the user by the rim 14 to balance the normal force $F_1$ and is equal but opposite to the normal force. The contact pressure $P_2$ of the rim 14 against the user is equal to this opposing force $F_2$ divided by the annular rim surface area 34, $A_2$, i.e., $P_2=F_2/A_2$ or $F_2=P_2A_2$. As the magnitude of the opposing force is equal to the magnitude of the formal force, $F_1=F_2$ and $P_1A_1=P_2A_2$. Therefore, if the rim surface area 34, $A_2$ is configured to be greater than or equal to the normal area 32, $A_1$ at the dome opening, then the contact pressure against the patient's skin will not exceed the magnitude of the vacuum within the dome 12, i.e., $P_2=P_1$. Similarly, the rim surface area 34, $A_2$ may be sized with respect to the normal area 32, $A_1$ so that the contact pressure $P_2$ is maintained below 20 mmHg when the vacuum pressure $P_1$ within the dome is maintained at less than 20 mmHg. Likewise, if the vacuum pressure is cycled, different area ratios may be used to optimize the therapeutic effects while minimizing the potential for damage to the soft tissue within the dome or beneath the rim.

As the soft tissue enlarges, the rate of enlargement increases due to a beneficial physical phenomenon. If the tissue only slightly protrudes into the dome as shown in FIG. 3 and as is typically the initial condition, then the surface area 30 under the dome is only slightly larger than the normal area 32 at the dome opening. Therefore, the vacuum pressure $P_1$ acts on a surface area 30 which approaches the minimal value of the normal area. As enlargement occurs, more tissue protrudes into the dome 12 as shown in FIG. 4 thereby providing more surface area 30 under the dome. Because the surface area 30 under the dome is larger, the area over which the vacuum pressure acts is larger. For a given pressure, the enlargement of the soft tissue is a function of the surface area. Therefore, the total rate of enlargement of the soft tissue increases as treatment continues because the surface area under the dome is ever increasing. In other words, with more tissue under the dome the tensile force $F_s$ is greater ($F_s=PA_s$) and the breast grows larger faster. This however has no effect on the opposing force, or for that matter the normal force, as the tensile force $F_s$ is a vector which must always sum into the normal force. In still other words, a unit of surface area enlarges at a constant rate for any given pressure, but as the soft tissue surface area under the dome increases, there are more units of surface area increasing at the constant rate. Therefore, the total rate of enlargement increases as treatment continues even though the vacuum pressure is not increased.

One specific embodiment includes a dome 12 configured to fit over a human breast as shown in FIGS. 1 and 2. This embodiment includes a rim 14 having a surface area 34 approximately equal to the normal area 32 of the dome opening thereby preventing medical complications to the soft tissue as long as the pressure is properly regulated within the dome 12. However, alternate embodiments having a rim 14 with a surface area 34 equal to or less than the normal area 32 of the dome opening may be used depending upon the amplitude of the vacuum pressure used and depending upon whether the vacuum pressure is constant or varied. The pressure reducing means 16 is located underneath the patient's breast, so that the apparatus 10 may be hidden under loose-fitting clothes. As with the general embodiment, the vacuum pump assembly 16 of this embodiment is preferably comprised of a vacuum pump 20 with a power source 22, a pressure sensor 24 and servomechanism 26 to drive and control the vacuum pump and to regulate the pressure within the dome 12.

As shown in FIG. 1, this specific embodiment may take the form of a bra 40 having two domes 12 spaced by a hinge 42. Straps 44 may be attached to the bra 40 to retain the bra 40 in place. A gasket 46 may also be included about the rim 14 to improve the patient's comfort and enhance the seal about the rim. In the preferred embodiment, this gasket 46 may be a silicone gel cushion or other soft, conforming type material. Petroleum jelly may also be used to supplement or supplant the gasket. A manual override 48 is included on the vacuum pump assembly 16 so that the patient or doctor may vary the pressure below the optimal level so as to be more comfortable. Although two vacuum pump assemblies 16 may be used, one depending from each dome 12 so as to provide different pressures in the domes, the preferred embodiment places the domes in fluid communication with a conduit 50. Two pump assemblies 16 may be desired to balance the size of two breasts as they are enlarged, as many women have differently sized breasts. Further, the pump may be replaced with a manually actuated pump such as a bulb-type pump.

A second specific embodiment is shown in FIG. 5 wherein the dome 12 is configured to fit over a human penis. As can be seen from the figure, this embodiment comprises essentially the same features as the bra embodiment described above. The principal differences between these embodiments are the configurations of the dome 12' and rim 14' as well as the positioning of the straps 44'.

Another alternate embodiment is shown in FIG. 6. In this embodiment, a sheet of material 60 is adhesively applied to the desired soft tissue using double-sided tape or other temporary adhesive 61. The sheet 60 is attached to the rim 14 so that a hermetic seal is formed between the sheet and the dome 12. The cavity 62 between the dome 12 and sheet 60 may be evacuated as in the first general embodiment through a port 64 to apply the tensile force to the soft tissue. This embodiment eliminates the potential for leakage between the rim 14 and the skin adjacent the rim by permitting the user to adhesively bond the sheet 60 to the soft tissue mass and to evacuate the cavity 62 to apply the tensile force. The adhesive 61 may comprise typical adhesives or glues, as well as, sticky gels or sheets of double-sided adhesive tapes. Further, the adhesive 61 may be an adhesive substance embedded in the sheet 60. The double-sided tape or other adhesive means 61 makes attachment more convenient as the tape may be removed from the flexible sheet 60 after each use and disposed. A new tape 61 may be applied to the sheet 16 before each application of the apparatus 10 to assure that slippage does not occur.

In each of the above-described embodiments, the gasket 46 attached to the rim 14 may be configured to distribute any shear forces generated between the skin and rim as the tensile force is applied. This shear force distribution may be accomplished with the use of a silicone gel or inflated membrane or bladder which has a thickness sufficient to allow its surface 70 adjacent the soft tissue to shift laterally with respect to the rim. In this way, the shearing force is distributed along the surface 70 adjacent the soft tissue so that the force is not concentrated at the edge 72 of the rim adjacent the dome. In addition to distributing the shear forces over a larger area, the gel or other flexible rim material provides a cushion to improve the user's comfort and inhibit contusions should an unintentional impact be applied to the dome.

In order to use the invention, the patient places the dome over the area of desired enlargement and adjusts the straps for comfort. Then the patient simply turns the vacuum pump on or actuates a manual pump to generate a vacuum. These apparatuses are intended to be worn 8–12 hours per day and can be worn during sleep. After several months, notable and long-term enlargement should occur. When the desired enlargement is achieved, the use of the device may be suspended. If additional enlargement is desired, then use may be continued. Occasional use or use at a reduced pressure may also be desired to maintain the desired enlargement.

There are various changes and modifications which may be made to the invention as would be apparent to those skilled in the art. However, these changes or modifications are included in the teaching of the disclosure and it is intended that the invention be limited only by the scope of the claims appended hereto.

What is claimed is:

1. An appliance for enlarging a patient's soft tissue, said appliance comprising a dome adapted to surround a portion of said patient's soft tissue, said dome being configured for supporting a vacuum pressure between the portion of said patient's soft tissue and said dome, the vacuum pressure applying a tensile force to the portion of said patient's soft tissue, a rim for supporting said dome against said tensile force, said rim being adapted to apply a contact pressure to a patient's skin in response to the tensile force applied to the portion of said patient's soft tissue, and said rim having a cross-sectional area sized so that upon application of the tensile force at a magnitude sufficient to enlarge the portion of said patient's soft tissue, the contact pressure applied to the patient's skin by said rim is below a level which causes permanent harm.

2. The appliance of claim 1 wherein said rim is sized to prevent the contact pressure applied to the patient's skin from exceeding 20 mmHg for a period of time sufficient to cause permanent harm to said skin.

3. The appliance of claim 2 wherein said rim is sized to prevent the contact pressure applied to the patient's skin from exceeding 20 mmHg when said vacuum pressure is equal to 20 mmHg.

4. The appliance of claim 3 wherein said dome has a projected normal area defined by the rim, said rim has a contact surface area which applies the contact pressure to the skin, and the rim contact surface area is substantially equal to the dome normal area.

5. The appliance of claim 1 further comprising a flexible sheet attached about the rim and at least partially spanning the dome, the flexible sheet being configured for bonding to said soft tissue.

6. The appliance of claim 5 wherein a vacuum is generated between said sheet and said dome to apply the tensile force to said patient's soft tissue.

7. The appliance of claim 5 further comprising a double-sided tape for bonding said flexible sheet to said soft tissue.

8. The appliance of claim 5 further comprising an adhesive for bonding said flexible sheet to said soft tissue.

9. The appliance of claim 8 wherein said adhesive substance is a film of adhesive gel.

10. In an appliance for applying a tensile force to a patient's soft tissue with a dome, the improvement comprising a rim at least partially surrounding said dome and having a surface adapted for contacting said patient's skin, said rim having a portion extending between the dome and the surface, said portion being adapted for contacting the patient's skin, said portion being sufficiently flexible to permit relative movement between the dome and the surface.

11. The improvement of claim 10 wherein the rim comprises a gel.

12. The improvement of claim 10 wherein the rim comprises an inflated bladder.

13. The improvement of claim 10 wherein the relative movement between the dome and the surface is generally in a direction parallel to said surface.

14. An appliance for enlarging a patient's soft tissue, said appliance comprising at least one dome adapted to surround a portion of said patient's soft tissue, a vacuum pump for lowering the pressure within said dome to thereby create a tensile force which is applied to the portion of said patient's soft tissue, and a regulator connected to said pump for cycling the amount of vacuum pressure inside said dome.

15. The appliance of claim 14 wherein said regulator includes a control connected to said vacuum pump for automatically cycling the vacuum pressure inside said dome between alternating periods of therapeutically effective vacuum pressures and vacuum pressures permitting perfusion of tissue underlying an edge of said dome.

16. A method of enlarging a patient's soft tissue comprising the steps of:

placing a dome over said soft tissue;

exerting a tensile force on the soft tissue, said force being applied at a value and for a period of time which when considered together will prevent damage from occurring to the soft tissue and will cause the soft tissue to enlarge; and exerting a contact pressure on an area at least partially surrounding the soft tissue, said pressure being applied at a value and for a period of time which when considered together will prevent damage from occurring to the area.

17. The method of claim 16 further comprising the steps of relieving and reapplying the tensile force and the contact pressure at intervals to prevent damage from occurring to the soft tissue and the area surrounding the soft tissue.

18. An appliance for enlarging a patient's soft tissue, said appliance comprising a dome adapted to surround a portion of said patient's soft tissue, said dome being configured for supporting a vacuum pressure between the portion of said patient's soft tissue and said dome, the vacuum pressure applying a tensile force to the portion of said patient's soft tissue, and a rim for supporting said dome against said tensile force, said rim having a sticky surface adapted to adhere to a patient's skin to thereby create and hold a pressure seal between said dome and said patient.

19. The appliance of claim 18 further comprising a gasket secured to said rim, said gasket having said sticky surface.

20. The appliance of claim 19 further comprising a strap attached to said dome for wrapping around said patient and holding said dome onto said patient.

21. The appliance of claim 20 wherein said appliance comprises a pair of said domes, said domes being oriented with respect to each other for placement over a woman's breasts.

22. The appliance of claim 21 wherein said tensile force comprises a pressure less than atmospheric pressure inside said domes as said appliance is applied to a patient.

23. The appliance of claim 22 wherein said each of said gaskets has a greater radial dimension than its associated dome.

24. The appliance of claim 23 wherein each of said rims has a greater radial dimension than its associated dome.

25. The appliance of claim 24 wherein each of said rims and its associated gasket has substantially the same radial dimension, and said radial dimension is sufficiently large to effectively support said domes without causing damage to any underlying soft tissue as said appliance is applied to said patient.

26. An appliance for enlarging a patient's soft tissue, said appliance comprising at least one dome adapted to surround a portion of said patient's soft tissue, said at least one dome being configured for supporting a vacuum pressure between the portion of said patient's soft tissue and said at least one dome, the vacuum pressure applying a tensile force to the portion of said patient's soft tissue, said at least one dome having a peripheral rim and an underlying gasket for supporting said at least one dome against said tensile force, and said gasket having a sticky surface adapted to adhere to a patient's skin to thereby create and hold a pressure seal between said at least one dome and said patient.

27. The appliance of claim 26 wherein two domes are included therein.

28. The appliance of claim 27 further comprising a strap attached to said domes for wrapping around said patient and holding said domes onto said patient, said domes being attached to each other.

29. The appliance of claim 28 wherein said domes are oriented with respect to each other for placement over a woman's breasts.

30. The appliance of claim 26 wherein said sticky surface is not sufficiently tacky to counteract said tensile force, and further comprising a strap attached to said at least one dome for wrapping around said patient and holding said appliance onto said patient in counteraction to said tensile force.

* * * * *